United States Patent [19]
Nasu et al.

[11] Patent Number: 5,616,228
[45] Date of Patent: Apr. 1, 1997

[54] CAPILLARY ELECTROPHORESIS APPARATUS FOR DETECTING EMITTED FLUORESCENCE FROM A SAMPLE WITHOUT EMPLOYING AN EXTERNAL LIGHT SOURCE DEVICE

[75] Inventors: Hisanori Nasu; Kenji Yamamoto, both of Yokohama; Hitoshi Fujimiya, Mobara, all of Japan

[73] Assignee: Hitachi Software Engineering Co., Ltd., Kanagawa-ken, Japan

[21] Appl. No.: 535,955

[22] Filed: Sep. 28, 1995

[30] Foreign Application Priority Data

Sep. 29, 1994 [JP] Japan .................................. 6-259079

[51] Int. Cl.$^6$ .................................................. G01N 27/26
[52] U.S. Cl. ........................ 204/603; 204/612; 204/452; 204/461
[58] Field of Search ........................... 204/182.8, 299 R, 204/180.1, 601, 603, 612, 451, 452, 461

[56] References Cited

U.S. PATENT DOCUMENTS

| | | | |
|---|---|---|---|
| 4,867,559 | 9/1989 | Bach | 356/73 |
| 5,221,454 | 6/1993 | Manian et al. | 204/299 R |
| 5,240,585 | 8/1993 | Young et al. | 204/299 R |
| 5,246,577 | 9/1993 | Fuchs et al. | 210/198.2 |

FOREIGN PATENT DOCUMENTS 61-173158  8/1986  Japan .

OTHER PUBLICATIONS

Fujiwara et al., Waveguide Capillary Flow Cell for Fluoremetry, Anal. Chem., 1988, 60, 1065–1068.

*Primary Examiner*—Donald R. Valentine
*Assistant Examiner*—Alexander Noguerola
*Attorney, Agent, or Firm*—Fay, Sharpe, Beall, Fagan, Minnich & McKee

[57] ABSTRACT

The electrophoresis apparatus has a capillary filled with gel for use in electrophoresis. A first buffer solution container is provided for storing a buffer solution and introducing a sample labelled with a fluorescent substance into an inlet of said capillary for electrophoresis. A second buffer solution container is provided for storing a buffer solution containing a luminous solution, into which said sample is continually introduced from an outlet of said capillary after electrophoresis. Electrophoresis means is provided for subjecting said sample to electrophoresis by applying a predetermined value of voltage to said gel through which said sample is being transferred while being electrophoresed. Light receiving means is disposed underneath the outlet of said capillary to read fluorescence emitted from said sample from bottom in a direction in which said sample is approaching closer. This electrophoresis apparatus has benefits in that it can read an electrophoresis pattern of a sample of a nucleic acid or a protein obtained by subjecting the sample to electrophoresis with a high sensitivity without requiring any expensive device structure such as a laser beam source system. Thus, it is cheaper than conventional systems requiring such a laser beam system and is easier to handle.

12 Claims, 4 Drawing Sheets

CAPILLARY ELECTROPHORESIS APPARATUS FOR DETECTING EMITTED FLUORESCENCE FROM A SAMPLE WITHOUT EMPLOYING AN EXTERNAL LIGHT SOURCE DEVICE

BACKGROUND OF THE INVENTION

1. Field of the Invention

The present invention relates to a capillary electrophoresis apparatus and, more particularly, to a capillary electrophoresis apparatus for reading an electrophoresis pattern obtained by subjecting nucleic acids or proteins to gel electrophoresis through a capillary with a high degree of sensitivity or resolution without requiring any special or expensive device such as a laser beam source.

2. Description of the Related Art

Heretofore, techniques for analysis by means of gel electrophoresis methods have been extensively utilized for the fragmentation and for the analysis of structures of protein acids and nucleic acids present as a polymer in a body of an animal or a plant. In many cases the gel electrophoresis method is utilized for experiments in which a sample can be procured beforehand in a very limited amount. Therefore, the analysis using the gel electrophoresis method requires a very high sensitivity to the detection of the sample.

In conventional techniques, a sample to be analyzed is first labelled with a radioactive isotope, the labelled sample is injected into a gel, and the resulting gel material is subjected to electrophoresis. After electrophoresis, the gel is attached to an X-ray film or the like for exposure to X rays to be emitted from the radioactive isotope labelled in the sample. After exposure of the gel material containing the labelled sample to the X-ray film or the like for a given period of time, the X-ray film is then developed, and the exposed pattern resulting from the radioactive isotope transfered onto the X-ray film is read as a gel electrophoresis pattern in order to analyze the structure of the proteins or nucleic acids of the sample.

The radioactive isotopes, however, are so hazardous that they should be handled and managed with extreme care and with high security. Recently, technologies for handling laser light and technologies of laser light sources, optical sensors and signal processing have greatly developed leading to the development of fluorescence detecting methods for detecting an electrophoresis pattern without requiring the use of such hazardous radioactive isotopes. The fluorescence detecting methods comprise labelling a sample with a fluorescent substance, subjecting the sample to electrophoresis, exciting the labelled fluorescent substance directly with a laser light source, and detecting the resulting fluorescent pattern, thereby resulting in the detection of the electrophoresis pattern.

Figure 4:
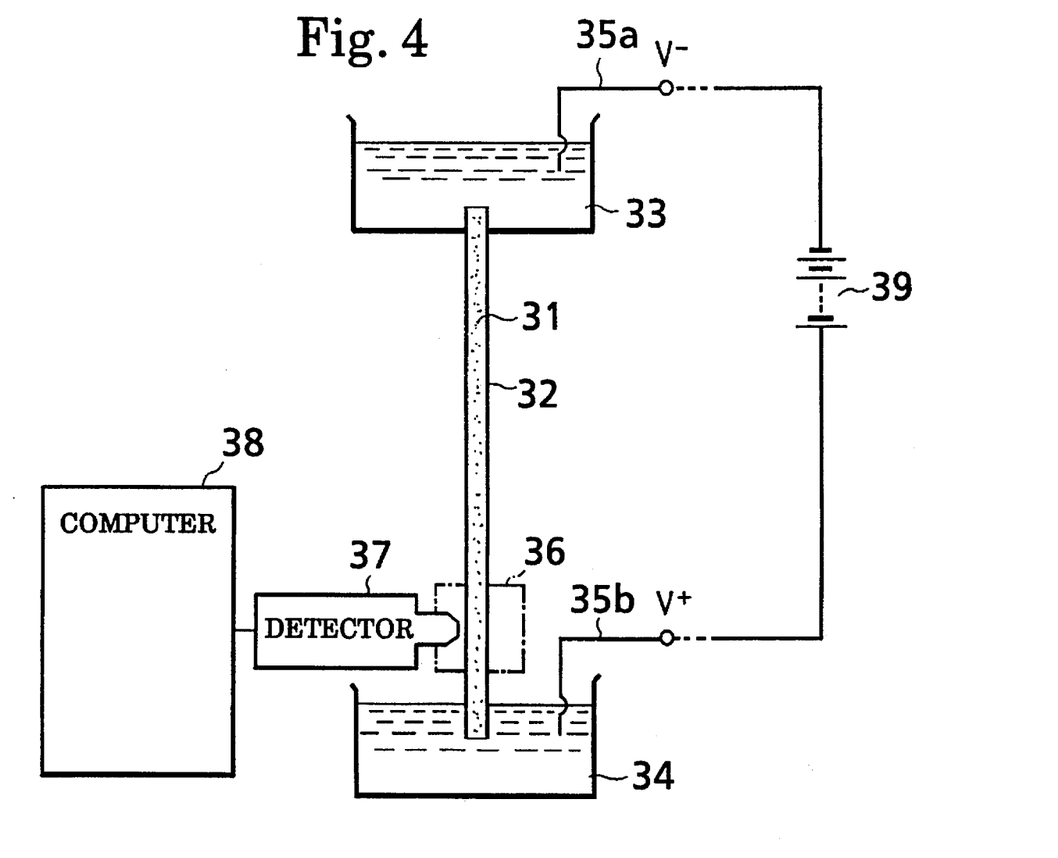
FIG. 4 is an abbreviated block diagram showing a brief structure of a conventional gel electrophoresis apparatus for a description of a method for the detection of a gel electrophoresis pattern using the fluorescence detection method.
Figure 5:
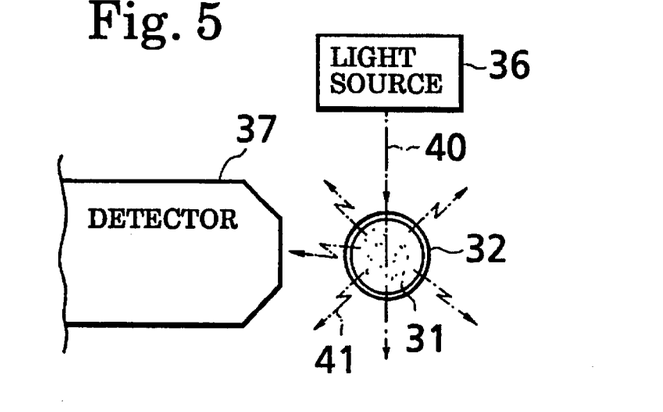
FIG. 5 is a view showing details of part of a fluorescence detection section of the conventional gel electrophoresis apparatus for a description of a gel electrophoresis pattern using the fluorescence detection method.

As an example of the method for reading an electrophoresis pattern by the fluorescence detecting method, which has initially been developed, there is known a method for determining the sequence of a DNA as disclosed in Japanese Patent Unexamined Publication No. 61-173,158. An outline of a fluorescence detecting method utilized for the DNA sequence determining method will be described with reference to FIGS. 4 and 5 which show a schematic representation of the method for the detection of a gel electrophoresis pattern by the fluorescence detecting method. FIG. 4 is a block diagram showing an outline of a gel electrophoresis apparatus and FIG. 5 shows the details of a portion of a fluorescence detecting section of the gel electrophoresis apparatus of FIG. 4.

First, a description will be made of the device structure of the gel electrophoresis apparatus with reference to FIG. 4. The gel electrophoresis apparatus comprises a gel 31 in which electrophoresis is performed, a fine tube 32 for retaining the gel 31, an upper buffer solution container 33 and a lower buffer solution container 34, between which electrical field is applied to the gel 31 held in the fine tube 32, a first electrode 35a, a second electrode 35b, a light source 36 for exciting a fluorescent substance labelled in the electrophoresed sample, a detector 37 for detecting the fluorescence emitted from the sample, a data processing section 38 for processing electrical signals transmitted from the detector 37 and converting the fluorescent signals into electrical signals, and an electric power supply 39 for applying electrophoresis electrical field between the first and second electrodes 35a and 35b.

Next, an operation of the gel electrophoresis apparatus will be described by example where a DNA sample is electrophoresed as an object of electrophoresis and an electrophoresis pattern of the DNA sample is read with the gel electrophoresis apparatus. The DNA sample is first labelled with a fluorescent substance and the labelled sample is introduced into the gel filled in the fine tube 32 from the upper buffer solution container 33, and electrophoresis voltage of from several kV to approximately 10 kV is applied from the electric power supply 39 between the first and second electrodes 35a and 35b. As the DNA has negative charges, they migrate toward the positive second electrode 35b upon application of the electrophoresis voltage and they eventually reach the position of the light source 36. Thereafter the fluorescent substance labelled in the DNA sample is excited in this position upon exposure to laser beams emitted from the light source 36, thereby emitting fluorescence. The fluorescence is received by the detector 37 to be converted into electrical signals. The electrical signals representing the fluorescence are transmitted to the data processing section 38. The data processing section 38 determines the sequences of the fragments separated by their molecular weights (electrophoresis pattern).

In this case, the detector 37 for receiving the fluorescence emitted from the sample in the gel 31 operates as follows. Namely, as shown in FIG. 5 which is a partial transverse sectional view (as looked down upon from above), when the sample migrates in the gel 31 and the sample reaches the position of laser beams 40 emitted from the light source 36, the fluorescent substance labelled in the DNAs of the sample in the gel 31 is excited with the laser beams 40, thereby resulting in the emission of fluorescence 41 that in turn is received by the detector 37. The detector 37 fetches the received fluorescence 41 in a photomultiplier and converts the fluorescence into electrical signals and transmits the electrical signals to the data processing unit 38. The data processing unit 38 is arranged such that the sequences of the fragments in the sample are determined by the molecular weights on the basis of the peak positions of the intensity of the fluorescence 41.

When they are employed as a sample, DNA fragments are labelled with the fluorescent substance so as to have different fluorescent wavelengths corresponding to their ingredients, and to determine the DNA sequences of the four bases simultaneously by only one fine tube. The fluorescent substance which can emit four different fluorescent wavelengths, may include, for example, fluorescein isothiocyanate (FITC), rhodamine isothiocyanate (EITC), tetramethylrhodamine isothiocyanate (TMRITC), and substituted rhodamine isothiocyanate (XRITC), respectively. Further, the gel electrophoresis apparatus of this type has a sensitivity to detection of DNAs in the order of $1\times10^{-16}$ mole as high as the method using radioactive isotopes, when argon ion laser having wavelength of 488 nm or 514 nm is employed.

In addition, the above example briefly alludes to an example in which luminescence can be caused by taking advantage of chemical reaction energy. However, the example does not specifically disclose any procedures of the elution from a gel material, a reaction with a luminous substance, the removal of an unnecessary labelling substance, and the like. Actually, there are many specific problems to be solved in embodying techniques, which may include, for example, procedures for the supply of a source of chemically luminescent material, the mixture of the luminous substance with a labelling substance, and the removal of the labelling substance after luminescence in order to prevent background noises from being caused by residual substances.

The electrophoresis methods can be applied to, for example, the diagnosis of hereditary diseases, the investigation of DNAs in determining suspects of crimes and the investigation of the relationship between a parent and a child, in addition to the determination of the DNA sequence. In the diagnosis of hereditary diseases, it is currently possible to distinguish even one base from samples on the basis of the difference between the electrophoresis patterns by taking advantage of the difference in the structure under specific conditions (e.g. temperature or pH as causing a minute difference in denatured states of DNA) by the substitution of the base or bases inherent in each hereditary disease, such as single strand conformation polymorphism. The investigation of DNA in, for example, determining a suspect of crime and a parent-child relationship is made by comparing the difference in electrophoresis distances by taking advantage of a deviation in DNAs (polymorphism) between individuals.

In such experiments, the base length of a DNA is approximately 1,000 bases or less in many cases, and the gel employed for electrophoresis is polyacrylamide gel. In the case where the base length is several thousands, agarose gel is employed. Further, a gel electrophoresis apparatus of a flat plate type is employed for the comparison of the electrophoresis pattern of a sample with a reference DNA electrophoresis pattern. With such an gel electrophoresis apparatus, the sample and the reference DNA sample are subjected to gel electrophoresis side by side for a ready reference to the difference between the two electrophoresis patterns.

These methods, however, require taking care in a number of ways including, for example, sustaining homogeneity of a gel with high stability and maintaining the uniformity of temperature on the electrophoresis plates during electrophoresis processes. In particular, a strict management of temperature using a thermostat is required in single strand conformation polymorphism. The strict management of temperature increases the cost of a device expensive and makes its size large because the flat plate electrophoresis apparatus consumes a large amount of power and the amount of heat evolved is great. With respect to this point, the management can be performed easier by an electrophoresis apparatus of a capillary type because such apparatus can make its electrophoresis section smaller in size.

However, the prior art electrophoresis apparatus for reading the electrophoresis pattern obtained by the fluorescence detecting method of conventional technology requires the use of a laser light source of a unique type corresponding to the wavelength at which the fluorescent substance is to be excited. The conventional electrophoresis apparatus suffers from various disadvantages. One disadvantage is that the cost of the laser light source, which amounts for the total cost of the apparatus, is so great that the cost of the apparatus itself becomes expensive as well. Further, laser light emitted from the laser light source has a high energy density even if it would scatter, so that there is the risk of causing disorders or abnormality of vision, such as dyschromatopsia or blindness, if the laser light were to enter the naked eye. Hence, such a laser light source should be handled with great care and should be incorporated in the electrophoresis apparatus with great attention paid to security from such laser light. This also leads to making the electrophoresis apparatus expensive.

SUMMARY OF THE INVENTION

It is an object of the present invention to provide a capillary electrophoresis apparatus which has such excellent characteristics that it can read an electrophoresis pattern obtained by subjecting nucleic acids or proteins to gel electrophoresis through a capillary with a high degree of sensitivity or resolution without requiring any special or expensive device such as a laser beam source, thereby rendering it less expensive in costs for manufacturing, and making it easier to handle.

It is another object of the present invention to provide a capillary electrophoresis apparatus which efficiently gathers fluorescence emitted from a fluorescent substance labelling an electrophoresed sample with a high degree of sensitivity or resolution.

It is a further object of the present invention to provide a capillary electrophoresis apparatus which has an optical system capable of selectively gathering objective light emitted from a sample in the vicinity of an outlet of the capillary by reducing the light from the sample remaining around an area in which the light emitted from the sample is read.

It is still a further object of the present invention to provide a capillary electrophoresis apparatus which has a passage for discharging a sample after reading in order to reduce background noises generated from the electrophoresed sample remaining around an area in which the light emitted from the sample is read.

In order to achieve the objects as described hereinabove, the present invention provides a capillary electrophoresis apparatus comprising: a capillary having gel for electrophoresis filled into a hollow portion thereof; a first buffer solution container for storing a buffer solution and introducing a sample labelled with a fluorescent substance capable of emitting fluorescence into the gel from an inlet of the gel contained in the capillary; a second buffer solution container for storing a buffer solution mixed with a luminous solution containing a light-emitting or luminous substrate capable of emitting light and introducing the electrophoresed sample discharged continually thereinto from an outlet of the gel contained in the hollow portion of the capillary; electrophoresis means for subjecting the sample in the gel to electrophoresis by applying a predetermined value of voltage to the gel contained in the hollow portion of the capillary; and light receiving means for receiving and reading fluorescence emitted from the sample from the bottom of the outlet of the capillary, the sample being introduced into the second buffer solution container. The light receiving means is disposed on the side facing the gel contained in the capillary to read the fluorescence emitted from the sample introduced into the second buffer solution container from the bottom of the capillary in a direction opposite to electrophoresis or development of the sample.

Further, the capillary electrophoresis apparatus according to the present invention is characterized in that the light receiving means is provided with a light gathering device capable of selectively gathering fluorescence in the vicinity of the outlet of the capillary.

Still further, the capillary electrophoresis apparatus is characterized by a first capillary having gel for use with separation of a sample by electrophoresis poured into a hollow portion thereof; a second capillary having gel for use in discharging the sample by electrophoresis poured into a hollow portion thereof; a first buffer solution container in which a buffer solution is stored and into which the sample labelled with a fluorescent substance is introduced from the inlet of the gel contained in the hollow portion of the first capillary; a second buffer solution container in which the buffer solution mixed with a light-emitting or luminous solution capable of emitting light and into which the electrophoresed sample is introduced continually from an outlet of the gel contained in the hollow portion of the first capillary; electrophoresis means for subjecting the sample to electrophoresis by applying a predetermined value of voltage to the gel contained in the hollow portions of the first capillary and the second capillary; and light receiving means for receiving and reading fluorescence emitted from the sample introduced into the second buffer solution container from the bottom of the outlet of the capillary.

The capillary electrophoresis apparatus according to the present invention is further characterized by a third buffer solution container which is provided for storing the sample discharged from the second buffer solution container through the second capillary through which the sample is transferred from an inlet of the second capillary to an outlet thereof by applying a predetermined value of voltage to the second capillary.

In the capillary electrophoresis apparatus according to the present invention having the features as described hereinabove, the capillary is poured with the gel for use in electrophoresis, the buffer solution is stored in the first buffer solution container, and the sample labelled with the fluorescent substance is introduced into the gel from the inlet of the gel in the capillary. Further, the buffer solution mixed with the light-emitting or luminous solution is stored in the second buffer solution container and the electrophoresed sample is introduced continually into the second buffer solution container from the outlet of the capillary. Upon electrophoresis of the sample with the electrophoresis means, the light-receiving means then receives and reads the fluorescence emitted from the sample introduced into the second buffer solution container from the bottom of the outlet of the capillary, the light-receiving means being disposed in the position facing the bottom of the outlet of the capillary from which the sample is being discharged.

As described hereinabove, the light-receiving means receives and reads the fluorescence emitted from the sample introduced into the second buffer solution container in the position facing the bottom of the outlet of the capillary. In other words, as the fluorescence emitted from the sample is received by the light-receiving means in the direction in which the sample emitting the fluorescence is being discharged, the light-receiving means can gather the fluorescence emitted from the fluorescent substance labelling the sample with a high degree of efficiency below the downwardly directed opening of the outlet of the capillary, thereby attaining a high level of sensitivity or resolution.

Further, for the capillary electrophoresis apparatus according to the present invention, the light-receiving means is provided with a light gathering device for selectively gathering the fluorescence emitted from the electrophoresed sample in the vicinity of the outlet of the capillary. The light gathering device can reduce the fluorescence emitted from the sample remaining in an area where the fluorescence from the remainder of the sample exerts adverse influences upon a degree of sensitivity to detection and selectively gather the fluorescence in the vicinity of the outlet of the capillary, thereby detecting the fluorescence emitted from the sample with a high degree of sensitivity or resolution.

Still further, the capillary electrophoresis apparatus according to the present invention is provided with the first capillary having the gel for use in electrophoresis filled into a hollow portion thereof; the second capillary having the gel for use in discharging the sample by electrophoresis filled into a hollow portion thereof; the first buffer solution container in which the buffer solution is stored and which leads the sample labelled with the fluorescent substance to the inlet of the gel in the hollow portion of the first capillary; the second buffer solution container in which the buffer solution mixed with the light-emitting or luminous solution is stored and into which the electrophoresed sample is introduced continually from the outlet of the first capillary; the electrophoresis means for subjecting the sample to electrophoresis by applying a predetermined value of voltage to the gel contained in the hollow portions of the first capillary and the second capillary; and the light-receiving means disposed to read the fluorescence emitted from the sample introduced into the second buffer solution container from the bottom of the outlet of the capillary.

Furthermore, the capillary electrophoresis apparatus according to the present invention comprises a third buffer solution container into which the sample discharged from the second buffer solution container and transferred through the gel contained in the second capillary is introduced by application voltage thereto. Thus, the gel in the second capillary serves as transferring the sample from the inlet of the second capillary in the second buffer solution container toward the third buffer solution container, after the electrophoresis has been finished. In other words, the second capillary may constitute a passage through which the sample is transferred and discharged from the second buffer solution container, thereby causing the sample to be discharged gradually after the sample has been subjected to electrophoresis. As a consequence, this configuration of the electrophoresis apparatus of the capillary type allows the sample remaining in the second buffer solution container to be reduced and the fluorescence emitted from the remaining sample can be reduced, thereby lowering background noises and improving sensitivity or resolution to detection of the fluorescence of the sample to be received by the light receiving means.

The capillary electrophoresis apparatus according to the present invention may also utilize light from the light-emitting or luminous solution capable of generating chemiluminescence as light for activating or exciting the fluorescence emitted from the fluorescent substance labelling the electrophoresed sample. For example, such a light-emitting or luminous solution may contain a luminous substrate that can produce an active intermediate substance emitting chemiluminescence. The employment of the light-emitting or luminous solution capable of generating chemiluminescence does not require laser beams and the optical energy of such an active intermediate substance may be absorbed by the fluorescent substance, thereby exerting a sufficient intensity of an activation or excitement action upon the fluorescent substance labelling the sample. As a result, the fluorescent substance of the sample is activated or excited to a sufficiently high level and generates fluorescence that in turn is detected by a light detecting device such as a photomultiplier, thereby providing an electrophoresis pattern having a satisfactory intensity of fluorescence and enabling the reading of the fluorescence at a sufficient degree of sensitivity and resolution.

The other objects, features and advantages of the present invention will become apparent in the course of the description that follows, with reference to the accompanying drawings.

DETAILED DESCRIPTION OF THE PREFERRED EMBODIMENTS

The present invention will be described in more detail by way of embodiments with reference to the accompanying drawings.

Figure 1:
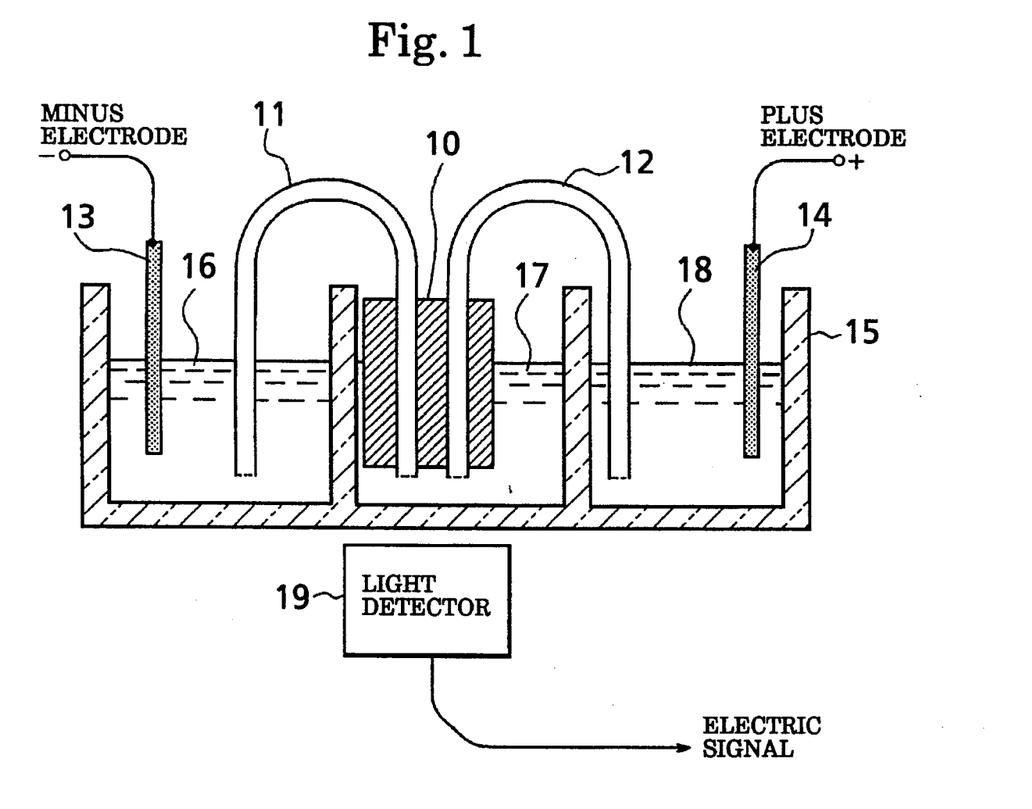
FIG. 1 is a block diagram showing an entire configuration of a capillary electrophoresis apparatus according to an embodiment of the present invention.

FIG. 1 is a block diagram showing an entire configuration of a capillary electrophoresis apparatus according to an embodiment of the present invention. In FIG. 1, reference numeral 10 denotes a support member for supporting a capillary, reference numeral 11 a first capillary having gel filled into a hollow portion thereof for use in separating a component from a sample by electrophoresis, reference numeral 12 a second capillary having gel filled into a hollow portion thereof for use in discharging the sample after separation by electrophoresis, reference numeral 13 a first electrode for applying voltage to the sample for separation by electrophoresis and for transferring the sample, reference numeral 14 a second electrode for applying voltage to the sample for separation by electrophoresis and for transferring the sample, like the first electrode 13, reference numeral 15 an electrophoresis container that is divided into three container sections in each of which a buffer solution is stored, reference numeral 16 a first buffer solution container section disposed on an inlet side of the sample, reference numeral 17 a second buffer solution container section disposed on an outlet side of the sample to be mixed with a light-emitting or luminous solution, reference numeral 18 a third buffer solution container section disposed on the outlet side of the second buffer solution container section 17 for discharging the sample, and reference numeral 19 a photodetector for detecting fluorescence emitted from the sample.

As shown in FIG. 1, the basic structure of the capillary electrophoresis apparatus according to the present invention comprises the electrophoresis container 15 consisting of the three container sections 16, 17 and 18, and made of a transparent material that can pass fluorescence; the first capillary 11 disposed to communicate the first buffer solution container section 16 with the second buffer solution container section 17, through which the sample is subjected to electrophoresis while being transferred therethrough; and the second capillary 12 disposed to communicate the second buffer solution container section 17 with the third buffer solution container section 18, through which the sample is transferred and discharged after separation by electrophoresis. The first capillary 11 is filled with the gel for separating the sample by electrophoresis and the second capillary 12 is filled with the gel for discharging the sample after having read the fluorescence of the sample. To each of the first and second capillaries 11 and 12, a predetermined value of voltage for electrophoresis is applied. As a result, the sample is separated by electrophoresis with the aid of the gel in the first capillary 11, and is then to be transferred into the second capillary 12 by electrophoresis with the aid of the gel in the second capillary 12.

In the second buffer solution container section 17, the buffer solution is mixed with a light-emitting or luminous solution containing a luminous substrate capable of exciting the fluorescent substance labelling the sample. Such a luminous substrate can provide the fluorescent substance of the sample with energy of an active intermediate substance, thereby exciting the fluorescent substance of the sample to generate fluorescence. The fluorescence emitted from the sample is then received and read by the light detector 19 disposed underneath the outlet of the first capillary 11 to provide an electrophoresis pattern of the sample.

As the fluorescent substance utilized as a label for the sample, there may be employed those as illustrated in the above description of the related art. In addition, there may be employed pigments capable of penetrating into double strands of DNAs and they may include, for example, ethidium homodimer, thiazole orange homodimer and oxazole yellow homodimer.

The light-emitting or luminous solution to be mixed with the electrophoresed sample in the second buffer solution container section 17 may contain a luminous substrate such as a chemically luminous substrate capable of generating chemiluminescence, a biologically luminous substrate capable of generating bioluminescence or the like. Among the chemically luminous substrates, there may be appropriately utilized a luminous substrate causing a chemical reaction with a peroxalic acid ester, which can form an active intermediate substance and provide a fluorescent substance with its energy, thereby generating chemiluminescence. The chemically luminous substrates emitting chemiluminescence by the chemical reaction with the peroxalic acid ester have been conventionally utilized as a source capable of exciting a fluorescent substance labelling DNAs to be used as a sample and efficiently generating chemiluminescence.

More specifically, for the embodiments according to the present invention, the luminous substrate may include, for example, a solution of an aryl oxalate in hydrogen peroxide using acetonitrile as a solvent and an imidazole as a catalyst.

As the aryl oxalates, there may be mentioned, for example, bis(2,4,6-trichlorophenyl)oxalate (TCPO), bis(4-nitro-2-(3, 4,6-trioxadecyloxycarbonyl)phenyl) oxalate (TDPO), bis(2, 4-dinitrophenyl)oxalate (DNPO) or the like.

Now, a description will be made of the procedures for subjecting the sample to electrophoresis with reference to FIG. 1.

A sample labelled with a fluorescent substance is poured into a hollow portion of the first capillary 11 from its inlet disposed in the first buffer solution container section 16. A predetermined intensity of voltage is applied between the first electrode 13 disposed in the first buffer solution container section 16 and the second electrode 14 disposed in the third buffer solution container section 18 from an electric power supply (not shown). As a result, electrophoresis voltage is applied between the inlet side and the outlet side of the gel in the first capillary 11, and likewise between the inlet side and the outlet side of the gel in the second capillary 12. The action by the electrophoresis voltage allows a movement of the sample through the first and second capillaries 11 and 12 by electrophoresis, while the sample is being separated in the gel through the first capillary 11.

The sample separated by electrophoresis with the aid of the gel filled in the first capillary 11 is transferred to the second buffer solution container section 17. In this container section 17, the buffer solution is mixed with the light-emitting or luminous solution containing the luminous substrate for exciting the fluorescent substance. The active intermediate substance of the luminous substrate contained in the light-emitting or luminous solution produces energy to excite the fluorescent substance of the sample, thereby causing the generation of fluorescence. The fluorescence emitted from the sample is detected by the light detector disposed underneath the second buffer solution container section 17, and is then converted into electrical signals.

Now, a description will be made of the operations of the electrophoresis apparatus of capillary type according to the present invention.

First, a sample containing DNAs is prepared and the DNAs are divided into fragments which are labelled with a fluorescent substance. The sample labelled with the fluorescent substance is then poured into the first capillary 11 that has been filled with gel for use in electrophoresis. The sample may be poured into the first capillary 11 directly through a syringe or indirectly by placing the first capillary 11 in a container containing the DNA fragments of the sample and applying voltage to the first capillary 11 to transfer the sample into the capillary on the basis of the principle of electrophoresis. After the sample has been transferred into the first capillary 11, it is then set to the electrophoresis apparatus as shown in FIG. 1, followed by the application of voltage in several kilovolts between the first electrode 13 and the second electrode 14 to start electrophoresis.

By the electrophoresis, the DNA fragments are moved through the first capillary toward the second buffer solution container section 17 because they have negative charges thereon in the buffer solution. As they reach the outlet side of the gel in the first capillary 11, the sample comes in touch with the luminous substrate of the luminous solution contained in the second buffer solution container section 17, and the active intermediate substance existing in the luminous substrate thereof provides energy to the fluorescent substance labelling the DNA fragments of the sample. As a result, the fluorescent substance generates fluorescence. The fluorescence emitted from the sample reaches the light detector 19 disposed under the second buffer solution container section 17, and the fluorescence detected by the light detector 19 is then converted into electrical signals.

In the capillary electrophoresis apparatus according to the present invention, the light detector 19 is disposed under the second buffer solution container section 17 and under the opening of the outlet of the first capillary 11. In other words, the light detector 19 looks toward the direction in which the sample is being discharged downward from the outlet of the first capillary 11 and approaching. More specifically, as shown in FIG. 1, the DNA fragments separated by electrophoresis flow downward from the outlet of the first capillary 11 into the buffer solution in the second buffer solution container section 17. Accordingly, the light detector 19 can detect fluorescence in the position immediately below the sample moving downwardly. This configuration has a merit that it can improve the efficiency of detection remarkably in comparison with the case where the detection is performed in the direction perpendicular to the sample moving direction.

Once the sample has been transferred into the second buffer solution container section 17, a portion of the DNAs emitting fluorescence spreads into the buffer solution in the second buffer solution container section 17; however, a majority of the sample is attracted by the electrophoresis voltage and transferred to the inlet side of the second capillary 12. The majority of the sample is transferred through the second capillary 12 to the third buffer solution container section 18. If the sample would spread greatly around the outlet of the first capillary 11 into the buffer solution in the second buffer solution container section 17, such a great dispersion of the sample may be reduced to a large extent, for example, by forming gel of a low concentration around the opening ends of the outlet of the first capillary 11 and the inlet of the second capillary 12 to allow the sample to move through such a gel from the outlet of the first capillary 11 to the inlet of the second capillary 12.

After the sample has been subjected to electrophoresis and the fluorescence emitted from the sample has been read, it is discharged from the second capillary 12 into the third buffer solution container section 18. When the sample reaches the inlet side of the second capillary 12 in the second buffer solution container section 17 with the aid of the action of electrophoresis, it is then pulled into the gel in the second capillary 12 from its inlet and transferred therethrough toward the outlet thereof and eventually into the buffer solution in the third buffer solution container section 18 by the action of electrophoresis. As a result, the sample is discharged from the second buffer solution container section 17. The sample may then be withdrawn from the third buffer solution container section 18 after the completion of electrophoresis. As this discharging system serves as removing the sample from the second buffer solution container section 17, particularly from an area close to the outlet of the first capillary 11, the light detector 19 can efficiently receive and read the fluorescence from the sample with high accuracy around the outlet of the first capillary 11 immediately after the sample has been transferred from the outlet of the first capillary 11 into the second buffer solution container section 17 without undergoing adverse influences or interference from background noises that may otherwise be generated from the sample remaining around the outlet thereof in the second buffer solution container section 17.

Now, another embodiment of the present invention will now be described, with reference to FIG. 2. This variant is directed to an electrophoresis apparatus of capillary type which selectively collects or gathers fluorescence emitted from a sample in order to improve a degree of sensitivity to detection.

Figure 2:
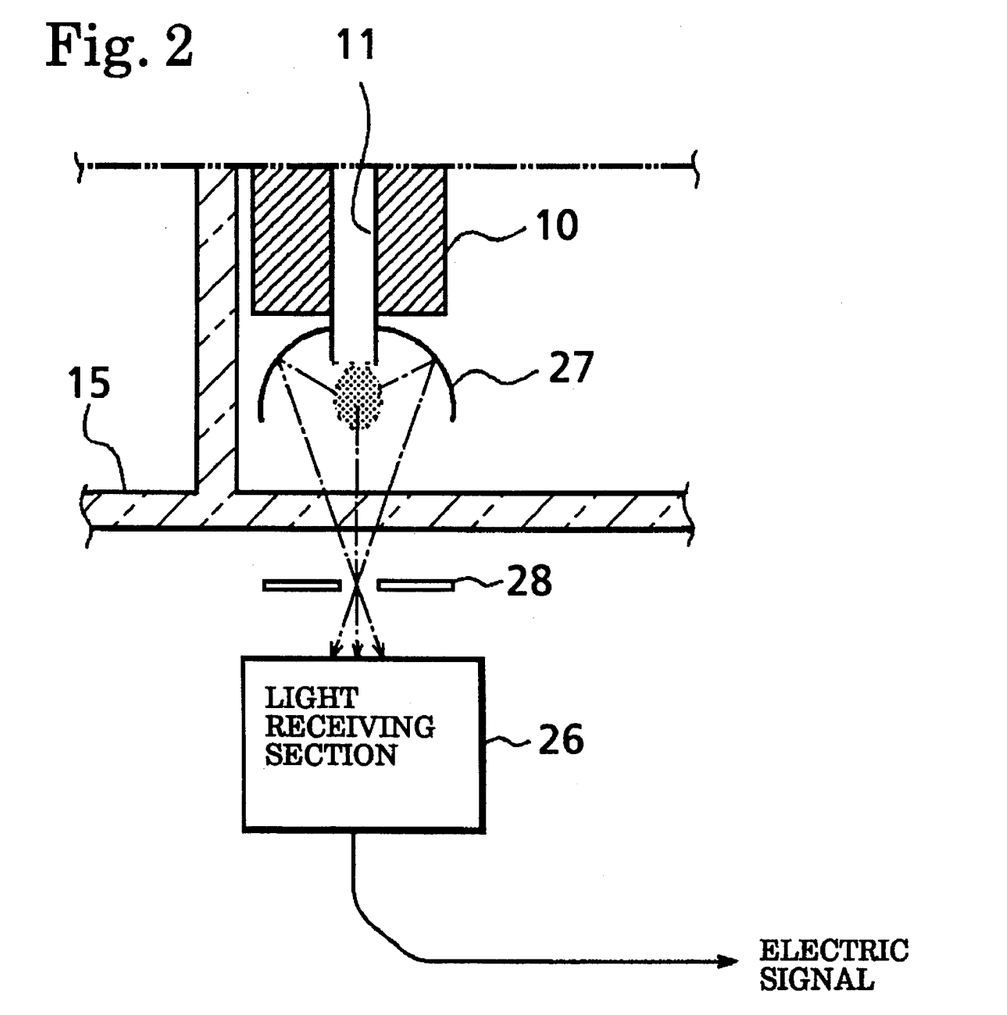
FIG. 2 is a view in section showing a light detecting device capable of providing a capillary electrophoresis apparatus with an improved degree of sensitivity according to another embodiment of the present invention.

As shown in FIG. 2, the electrophoresis apparatus of the variant comprises a support member 10 for supporting capillaries, a first capillary 11, a light-receiving section 26 consisting of a photomultiplier, a concave mirror 27 and an iris 28.

In the embodiment shown in FIG. 2, the concave mirror 27 is disposed at the outlet of the first capillary 11 from which the sample is transferred outside from the outlet thereof. As the concave mirror 27, there may be utilized a parabolic mirror or an oval-shaped concave mirror. The concave mirror 27 can function to collect fluorescence with high efficiency. When the oval-shaped concave mirror is employed as the concave mirror 27, the iris 28 is disposed in the focal position thereof. Only the fluorescence around the outlet of the first capillary 11 can be gathered by the oval-shaped concave mirror and a degree of sensitivity to detection can be improved without undergoing any adverse influence from background noises to be caused by the remainder of the sample around the outlet of the first capillary 11. Further, it should be noted herein, as a matter of course, that similar effects can be achieved when a convex lens having the focus on the portion generating fluorescence is disposed in front of the light-receiving section 26.

When samples labelled with a plurality of fluorescent substances are to be electrophoresed concurrently, their different kinds of fluorescence can also be read simultaneously, for example, by placing an optical filter before or behind the iris 28. The disposition of the optical filter allows the different kinds of fluorescence to be received and read efficiently in accordance with their respective wavelengths. As the optical filter, there may be employed a rotary multi-filter with plural sheets of optical filters mounted on a rotary member connected to a motor. The rotation of the rotary multi-filter enables the fluorescence having a predetermined wavelength to be read through the corresponding optical filter mounted on the rotary member, thereby allowing the light-receiving section to read it selectively. This system can concurrently read plural electrophoresis patterns of the different samples labelled with different kinds of fluorescent substances.

In addition, a description will be made of another embodiment of the capillary electrophoresis apparatus according to the present invention with reference to FIGS. 3A and 3B. As will be apparent from the description of the previous embodiments, the buffer solution filled in the second buffer solution container section 17 is mixed with the light-emitting or luminous solution containing the luminous substrate; however, the luminous substrate has its own life and its life is not long enough to last, for example, until a sequence of bases of a protein is to be analyzed. In other words, the electrophoresis apparatus depends upon the life of the luminous substrate contained in the light-emitting or luminous solution in the second buffer solution container section 17 and a period of time during which to operate the electrophoresis apparatus is restricted in this sense. For example, when a sequence of bases of a protein is to be analyzed, the electrophoresis is expected or required to be continued over a long period of time. However, there is the risk that the life of the luminous substrate would not last until the analysis of such a base sequence has been finished, unless any fresh supply of the luminous solution is added. In order to allow the life of the luminous substrate to last until the completion of the electrophoresis, it is useful to add a fresh supply of the luminous substrate to the second buffer solution container section 17 from outside in an automated way during electrophoresis.

Figure 3A:
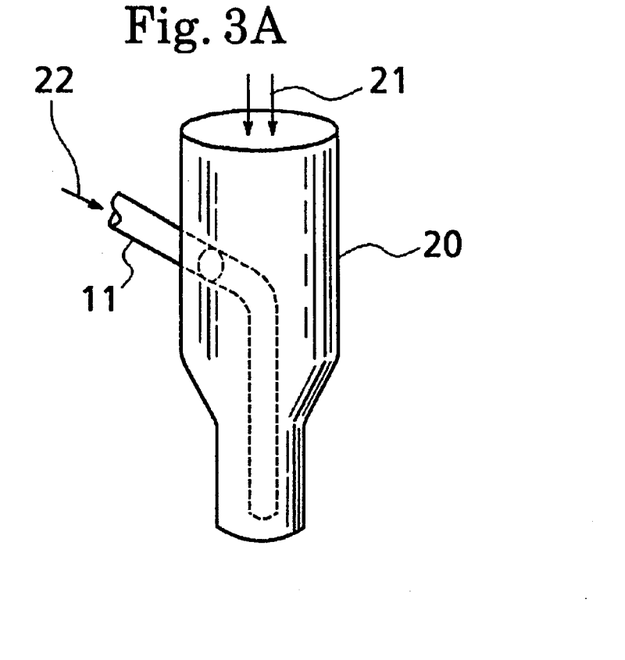
FIG. 3A is a view showing a supply means for feeding a fresh supply of a luminous solution in accordance with another embodiment of the present invention.
Figure 3B:
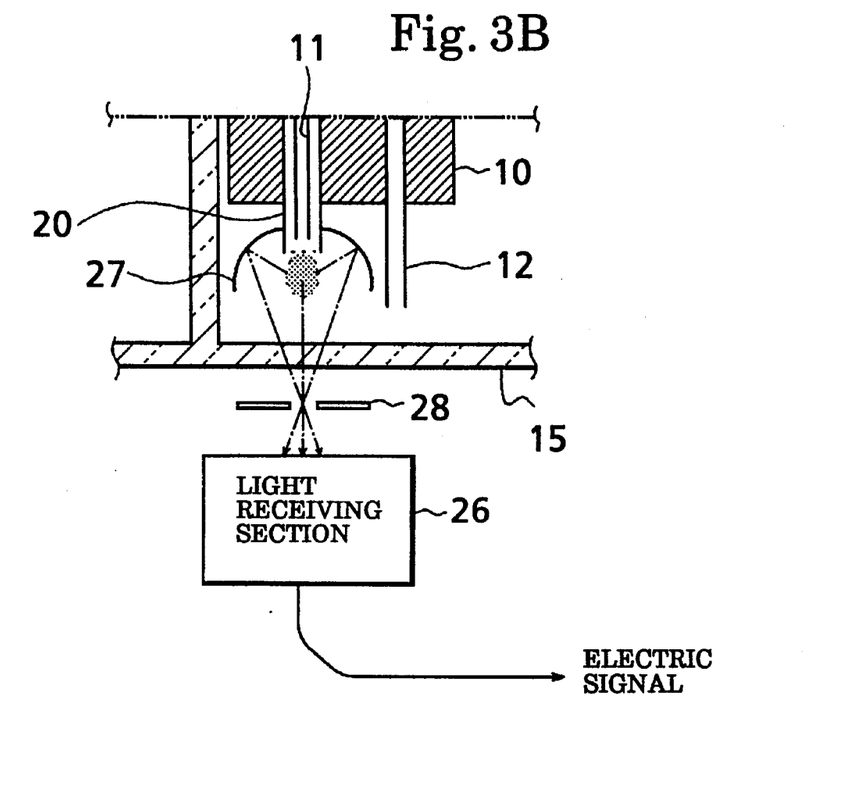
FIG. 3B is a view in section showing the supply means of FIG. 3A.

In order to allow an automated addition of fresh amounts of the luminous substrate to the second buffer solution container section 17, as shown in FIGS. 3A and 3B, the capillary electrophoresis apparatus according to another embodiment of the present invention comprises, among others, a support member 10 for supporting capillaries, a first capillary 11, a second capillary 12, a pipe 20 functioning as a tube for supplying additional amounts of a luminous solution, a fluorescence receiving section 26 composed of a photomultiplier, a concave mirror 27 and an iris 28. In FIG. 3A, reference numeral 21 denotes a passage of the luminous solution and reference numeral 22 denotes a passage of DNA fragments as a sample.

More specifically, as shown in FIG. 3A illustrating a supply portion for supplying additional amounts of a fresh luminous solution for the capillary electrophoresis apparatus according to another embodiment of the present invention, the pipe 20 encloses the outlet portion of the first capillary 11 in such a way that an outlet of the pipe 20 is located to allow fresh amounts of the luminous solution to be mixed with the sample around the outlet of the first capillary 11 immediately after the electrophoresed sample has been discharged from the outlet of the first capillary 11 into the second buffer solution container section 17. In other words, as shown in FIG. 3A, the sample passes through the first capillary 11 in the direction as indicated by arrow 22 and it is transferred into the second buffer solution container section from the outlet of the first capillary 11. Likewise, the fresh amount of the luminous solution flows through the passage of the pipe 20 as indicated by arrow 21 and transferred into the second buffer solution container section, too, in the position close to the position in which the sample has been transferred into the second buffer solution container section. As the sample containing the DNA fragments labelled with the fluorescent substance is transferred from the outlet of the first capillary 11 into the second buffer solution container section 17, they are allowed to come into contact with the luminous substrate mixed with the buffer solution filled therein, thereby causing the luminous substrate to activate or excite the fluorescent substance labelling the DNA fragments and, as a consequence, causing the fluorescent substance thereof to give out fluorescence. This system enables the sample to be always mixed with a fresh supply of the luminous substrate, thereby allowing the sample to continue giving out fluorescence and reading the fluorescence in a steady manner, while keeping a high sensitivity, even if the electrophoresis for a sequence of DNAs would be continued for a long period of time.

As described hereinabove, when the pigment such as ethidium homodimer, thiazole orange homodimer or oxazole yellow homodimer is employed, it is not required to label the sample with a fluorescent substance in advance. Such a pigment is held between the double strands of the DNA in the stage that it has been eluted after electrophoresis and light is given out due to changes of luminous efficiency. Hence, it can likewise give out light merely when it is mixed with a buffer solution container containing a luminous substrate as described hereinabove.

As described hereinabove, the capillary electrophoresis apparatus according to the present invention can read an electrophoresis pattern in a stable manner without using an expensive and special device such as a laser beams source because the apparatus can excite a sample and cause the fluorescent substance of the sample to give out fluorescence by a reaction energy created by a chemical reaction. This electrophoresis apparatus can be manufactured at cheaper costs than conventional ones using expensive and special devices. Further, the electrophoresis apparatus can selectively and efficiently collect the fluorescence without undergoing any adverse influences from background noises by mounting a concave mirror around the outlet of the capillary in which electrophoresis is carried out. Furthermore, the capillary electrophoresis apparatus is provided with the second capillary for discharging the sample after completion of separation of the sample by electrophoresis, thereby enabling the sample to be discharged from the container in which the fluorescence is read soon after the reading of the fluorescence has been finished. This can greatly reduce an occurrence of background noises that may otherwise be caused by the sample remaining in the container. This leads to the reading of an electrophoresis pattern with a high sensitivity and accuracy.

What is claimed is:

1. A capillary electrophoresis apparatus comprising:

a capillary having a hollow portion filled with a gel for use in electrophoresis;

a first buffer solution container for storing a buffer solution and for introducing a sample labelled with a fluorescent substance into an inlet of said capillary for separation of said sample by electrophoresis;

a second buffer solution container for storing a buffer solution containing a luminous solution, into which said sample is continually introduced from an outlet of said capillary after separation of said sample by electrophoresis;

electrophoresis means for subjecting said sample to electrophoresis by applying a voltage to said gel through which said sample is being transferred into said second buffer solution container; and light receiving means disposed underneath the outlet of said capillary to read fluorescence emitted from the fluorescent substance labelling said sample from under the outlet of said capillary from which said sample is downwardly discharged.

2. A capillary electrophoresis apparatus according to claim 1, wherein said light receiving means faces an opening of the outlet of said capillary, wherein said opening faces the bottom of the second buffer solution container.

3. A capillary electrophoresis apparatus according to claim 1, wherein said light receiving means is provided with a light collecting device capable of gathering the fluorescence emitted from the fluorescent substance of said sample only in the vicinity of the outlet of said capillary in said second buffer solution container.

4. A capillary electrophoresis apparatus according to claim 3, wherein said light collecting device is a concave mirror.

5. A capillary electrophoresis apparatus according to claim 3, wherein said light collecting device is a combination of an oval-shaped concave mirror with an iris.

6. A capillary electrophoresis apparatus comprising:

a first capillary having a hollow portion filled with a gel for use in electrophoresis of a sample;

a second capillary having a hollow portion filled with a gel for use in removing said sample by electrophoresis;

a first buffer solution container for storing a first buffer solution and introducing said sample labelled with a fluorescent substance into the gel filling said first capillary from an inlet of said first capillary;

a second buffer solution container for storing a second buffer solution and introducing said sample separated through said first capillary by electrophoresis into the second buffer solution from an outlet of said first capillary;

electrophoresis means for subjecting said sample to electrophoresis to the gel filling said first capillary and said second capillary by applying a voltage; and light receiving means disposed underneath said second buffer solution container for receiving and reading fluorescence emitted from the fluorescent substance labelling said sample introduced into said second buffer solution container, wherein the sample flows in a downward direction from the outlet of said first capillary.

7. A capillary electrophoresis apparatus according to claim 6, further comprising a third buffer solution container into which said sample is introduced from said second buffer solution container through the gel filling said second capillary and to which a voltage is applied.

8. A capillary electrophoresis apparatus comprising:

a first capillary having a hollow portion filled with a gel for use in electrophoresis;

a second capillary having a hollow portion filled with a gel for use in removing by electrophoresis;

a first buffer solution container for storing a first buffer solution and introducing a sample labelled with a fluorescent substance into the gel filling said first capillary from an inlet of said first capillary;

a second buffer solution container for storing a second buffer solution and introducing said sample separated by electrophoresis into the second buffer solution from an outlet of said first capillary;

pipe means enclosing an outlet portion of said first capillary for supplying a luminous solution to the second buffer solution filling said second buffer solution container;

electrophoresis means for subjecting said sample to electrophoresis by applying a voltage to the gel filling said first capillary and said second capillary; and a light receiving means for receiving and reading fluorescence emitted from said sample discharged downward from the outlet of said first capillary and introduced into said second buffer solution container from a bottom of said first buffer solution container in a direction in which said sample separated in said first capillary flows downward from the outlet of said first capillary.

9. A capillary electrophoresis apparatus according to claim 8, wherein said light receiving means is disposed to read the fluorescence emitted from the fluorescent substance labelling said sample discharged downward from the outlet of said second capillary and introduced into said second buffer solution container in a position facing a direction in which said sample advances in the second buffer solution of said second buffer solution container from the outlet of said first capillary.

10. A capillary electrophoresis apparatus as recited in claim 8, wherein said light receiving means is provided in the vicinity of the outlet of said first capillary with a light gathering device for gathering the fluorescence emitted from the fluorescent substance labelling said sample.

11. A capillary electrophoresis apparatus according to claim 10, wherein said light gathering device is a concave mirror.

12. A capillary electrophoresis apparatus according to claim 10, wherein said light gathering device is a combination of an oval-shaped concave mirror with an iris.

* * * * *